United States Patent [19]

Yuta

[11] Patent Number: 5,796,632
[45] Date of Patent: Aug. 18, 1998

[54] METHOD FOR CONVERTING INFORMATION OF PERIPHERAL SPACE OF A THREE-DIMENSIONAL COMPOUND STRUCTURE INTO NUMERICAL DATA AND METHOD FOR CONVERTING INTERACTIONS BETWEEN A THREE-DIMENSIONAL COMPOUND STRUCTURE AND PERIPHERAL SPACE INTO NUMERICAL DATA

[75] Inventor: Kohtaro Yuta, Kawasaki, Japan

[73] Assignee: Fujitsu Limited, Kawasaki, Japan

[21] Appl. No.: 546,138

[22] Filed: Oct. 20, 1995

[30] Foreign Application Priority Data

Oct. 20, 1994 [JP] Japan ................................. 6-255023

[51] Int. Cl.$^6$ ................................................. G06F 19/00
[52] U.S. Cl. ....................................... 364/496; 364/578
[58] Field of Search ................................ 364/496, 497, 364/578

[56] References Cited

U.S. PATENT DOCUMENTS

| | | | |
|---|---|---|---|
| 5,025,388 | 6/1991 | Cramer | 364/496 |
| 5,265,030 | 11/1993 | Skolnick | 364/496 |
| 5,353,236 | 10/1994 | Subbiah | 364/496 |
| 5,438,526 | 8/1995 | Itoh et al. | 364/578 |
| 5,448,498 | 9/1995 | Namiki et al. | 364/496 |
| 5,526,281 | 6/1996 | Chapman et al. | 364/496 |

OTHER PUBLICATIONS

Edelsbrunner et al. "Measuring proteins and voids in proteins," Proc. of 28th Annual Hawaii Conf. on System Science, vol. 5, 1995, pp. 256–264, no month.

Primary Examiner—Ellis B. Ramirez
Assistant Examiner—M. Kemper
Attorney, Agent, or Firm—Staas & Halsey

[57] ABSTRACT

A method for converting information of a peripheral space of a three-dimensional compound structure into numerical data is disclosed. This method comprises the steps of designating a peripheral region that includes the entire three-dimensional structure of a compound on the periphery thereof, designating a plurality of small regions in the peripheral region, generating a plurality of points in the peripheral region, calculating the interaction between the three-dimensional structure of a compound and each of points at least included in the points as numerical data so as to allocate the numerical data to corresponding individual points, and determining at least one of numerical data that represents each of the small regions corresponding to the numerical data allocated to each of the individual points. After a representative value of each small region is obtained, the representative value is supplied to a portion that performs various analyzing techniques such as the linear multiple regression method without any statistical defects.

16 Claims, 21 Drawing Sheets

METHOD FOR CONVERTING INFORMATION OF PERIPHERAL SPACE OF A THREE-DIMENSIONAL COMPOUND STRUCTURE INTO NUMERICAL DATA AND METHOD FOR CONVERTING INTERACTIONS BETWEEN A THREE-DIMENSIONAL COMPOUND STRUCTURE AND PERIPHERAL SPACE INTO NUMERICAL DATA

BACKGROUND OF THE INVENTION

1. Field of the Invention

The present invention relates to a method for converting information of a peripheral space of a three-dimensional compound structure into numerical data, and to a method for converting interactions between a three-dimensional compound structure and its peripheral space into numerical data, for use in such research fields of "SAR: Structure-Activity Relationships" and "SPR: Structure-Property Relationships" for evaluating the activities and physico-chemical properties that compose chemicals, such as drugs and agro-chemicals.

2. Description of the Related Art

In studies of the correlations between structure-activities and structure-properties, it is important to convert compound structures into numerical data (parameters). Only in the case, when the numerical data is obtained, can various chemical problems be statistically solved. In particular, the recent advancement of molecular modeling technologies (that are involved in the scientific field for calculating three-dimensional structures of compounds) allows three-dimensional structures of compounds to be easily obtained. In addition, the correlations between a structure and activity and the correlation between a structure and physico-chemical properties have advanced from analyses of one-dimensional and two-dimensional structures of compounds into more complicated analyses that deal with three-dimensional structures. At present, not only simple three-dimensional structures, but also the interactions between the three-dimensional structures of compounds and atoms in the peripheral space of the compounds are becoming important research themes for evaluating relationships between drugs and receptors. Based on the advancement of such studies, effective techniques for converting the information of three-dimensional structures of compounds into numerical data (three-dimensional parameters), and effective techniques for converting the interaction between the information of three-dimensional structures of compounds and atoms in the peripheral space of the compounds have been required.

Thus far, various types of information of three-dimensional structures of compounds have been proposed and practically used. For example, the STERIMOL parameter has been proposed. In the STERIMOL parameter, sterical structures of homologous substituents are three-dimensionally defined and converted into numerical data. In addition, molecular moment information is known. In the molecular moment information, a compound is placed in a three-dimensional box and the values of the X, Y, and Z axes and the ratios thereof are obtained so as to define the shape of the entire compound. As a three-dimensional parameter that has recently been proposed, the region parameter is known. In the region parameter, a three-dimensional compound is divided into three-dimensional regions and converted into numerical data corresponding to the information of the divided partial structures based on various criteria. Moreover, the CoMFA parameter is also known. In the CoMFA parameter, the peripheral space of a compound is divided by a three-dimensional lattice and steric interaction energy and electrostatic interaction energy at each lattice intersection are calculated and used as three dimensional parameters. Since various types of three-dimensional parameters have been proposed, research studies of the correlation between a three-dimensional structure and activity using these parameters has been widely employed.

Conventionally, techniques for converting three-dimensional structures into numerical data have been mainly employed. A typical example of these techniques is the technique using the above-mentioned STERIMOL parameter. FIG. 1 shows an example of the STERIMOL parameter. With this parameter, "the information of a three-dimensional shape" of a substituent of compound is converted into numerical data.

Thus far, there have been many techniques for converting the information of structures of three-dimensional compounds into numerical data. However, until now, an effective technique for converting "the environmental information of a peripheral space" of a three-dimensional compound into numerical data has not been proposed. Nevertheless, in 1988, a technique in which electrostatic interaction energy and steric interaction energy in the periphery of a three-dimensional compound are represented as values at each intersection of a three-dimensional lattice was proposed, so as to study the relationships between the drugs and receptors. Moreover, an analyzing technique using the PLS (Partial Least Squares) method that reduces many dimensions of data into fewer dimensions was proposed, so as to solve the statistical problems. The method for obtaining the correlation between a three-dimensional structure of a compound and biological activity using the information of the periphery of a three-dimensional compound was patented as the CoMFA approach (Comparative Molecular Field Analysis) (U.S. Pat. No. 5,025,388). FIG. 2 is a schematic diagram showing three-dimensional information of a compound obtained by the CoMFA approach.

As shown in FIG. 2, in the CoMFA approach a peripheral region of a three-dimensional compound 1 was surrounded by a three-dimensional lattice 2. Various parameters (such as a point charge for electrostatic interaction energy and repulsive potential-energy for van der Waals interaction) are assigned to each intersection of the lattice points as numerical data. Thus, since each intersection corresponds to one-dimensional data, the generated data shall have very many dimensions. For example, when each of the X, Y, and Z axes is separated by 10 lattice points, the final number of data dimensions is as high as 1000 ($=10^3$).

On the other hand, with respect to the relationships between a three-dimensional structure and activity, a technique other than the CoMFA approach has been proposed by the inventors of the present invention. This technique was applied for a prior patent of the present invention as the Japanese Patent Laid-Open Publication No. 6-332996. In this technique, a three-dimensional structure of a compound is divided into smaller regions. A three-dimensional partial structure of a compound in each of the small regions is converted into numerical data derived by various algorithms and mathematical methods. With the parameter obtained from the partial structure, it is easy to do 3-D QSAR studies. In this approach, an analysis can be performed without the analytical defect intrinsic to the CoMFA method (this defect will be discussed later).

When the technique for obtaining the correlation between a partial structure and biological activity using parameters is established, the parameters of the partial structure become an important matter. The kind of information which is included in the partial structure of the prior art of the present invention is only related to structure of the compounds used. Thus, there is no meaning to converting the information of the interaction between a compound and its peripheral environment into parameters. As the techniques for obtaining the correlation between a three-dimensional structure and activity using the parameter of the partial structure have improved, the necessity for the parameters that include the information between a three-dimensional structure of a compound and its peripheral environment has become stronger.

Only the above-described CoMFA approach is a technique for converting peripheral information of a three-dimensional structure of a compound into numerical data in the field of studying the correlations between a three-dimensional structure and the biological activity (3D-QSAR). However, the CoMFA approach has a critical problem in the process of reducing the dimension of the numerical data used. This problem results from statistical restrictions of using a linear multiple regression for obtaining the correlation between a structure and activity, rather than the process for converting information of a three-dimensional space into numerical data.

In other words, when an applying a linear multiple regression to analytical problem, there are several restrictions for maintaining statistical reliability. Among these, the most important restriction is the relationship between the number of samples and the number of dimensions of the numerical data used. To maintain the reliability of the analysis, the following equation (1) should be satisfied.

$$\text{[number of samples/number of dimensions of used numerical data]} \geq 6 \quad (1)$$

In the 3D-QSAR approach, the number of compounds (samples) used for obtaining the correlation between a structure and activity is very small (several tens to a hundred). Thus, the number of numerical data is at most a few to several tens. Consequently, the information of a peripheral space of a three-dimensional structure should be converted into numerical data fulfilling such restrictions.

When the peripheral information of a compound is converted into numerical data by the CoMFA approach, the entire three-dimensional space that surrounds the compound is divided into small portions. When each X, Y, and Z axis of three-dimensional space is divided to ten equal portions, the amount of generated data is 1000 ($=10^3$). Consequently, in the CoMFA method, 1000 dimensions of data should be reduced to several dimensions by the PLS method so as to perform linear multiple regression with a statistically high reliability.

However, the forced reduction of dimensions by the PLS method may be successful as a process. Nevertheless, it is not successful from the viewpoint of studying relationships between a structure and biological activity. In other words, when the number of dimensions are reduced by the PLS method, the information included in the used data is completely changed. Thus, the information obtained from the analytical result of the linear multiple regression method decreases and becomes ambiguous. Consequently, the most important process of 3D-QSAR study for determining relationships between a structure and activity cannot be performed, and this is the fatal defect of the CoMFA approach.

In other words, as disadvantages of an analysis using a small dimensional data derived from the PLS method, 1) it increases the difficulty of picking up important information imbedded in the numerical data used and 2) it becomes impossible to discuss the values and signs of the coefficients of the regression equation. The regression equation obtained from the conventional linear multiple regression method is given by the equation (2). On the other hand, the regression equation obtained using the CoMFA approach using the PLS method is given by the equation (3). In other words, in the regression equation obtained using the CoMFA approach, the coefficient of each parameter is lost. More accurately, although the coefficient of each parameter is not actually lost, since the information of the coefficient of each parameter cannot be used for evaluating the regression equation, the resultant equation is substantially equivalent to the equation (3). This is the biggest defect for the 3D-QSAR study using the CoMFA approach.

$$Y = A1 \times 1 + A2 \times 2 + \ldots + An \times n + \text{constant} \quad (2)$$

$$Y = (\alpha 1)P1 + (\alpha 2)P2 + \ldots + (\alpha n)Pn + \text{constant} \quad (3)$$

P1–Pn: generated by the PLS method

On the other hand, in the technique for obtaining the correlation between a three-dimensional structure and activity using the parameter derived from the above-described partial structural region (namely, the prior art invented by the inventors of the present invention), the information of the partial structure of compound is effectively converted into numerical data. In this technique the amount of generated numerical data is very small. Therefore, this technique does not need any reduction operation of demensions such as the PLS method used in the CoMFA. But, interactions between the compound and its peripheral space, such as steric or electrostatic interactions, cannot be handled by this technique.

However, as techniques for finding the correlation between a structure and activity have advanced, it becomes very important to precisely obtain the information of the interactions between a compound structure and the peripheral environment. Thus, it has been desired to develop a new technique for solving the above-described problem (namely, a technique for converting the interactions between a structure of compound and its peripheral space into numerical data of few dimensions to avoid statistical problems).

SUMMARY OF THE INVENTION

An object of the present invention is to accomplish a technique for obtaining the correlation between a structure and activity using information about steric, electrostatic and some other interactions which we obtained from the peripheral space of a three-dimensional compound structure, and for satisfactorily performing this technique using a linear multiple regression method or the like.

Another object of the present invention is to accomplish a technique for obtaining information of various interactions between a three-dimensional compound structure and the peripheral environment as numerical data.

A first aspect of the present invention is a method for converting information of a three-dimensional compound structure into numerical data, comprising the steps of (1) designating a peripheral region that includes the entire three-dimensional compound structure within the periphery thereof, (2) designating a plurality of small regions in the peripheral region, (3) generating a plurality of points in the peripheral region, (4) calculating the interactions between the three-dimensional compound structure and each of points at least included in the points as numerical data so as to allocate the numerical data to corresponding individual points, and (5) determining at least one of numerical data that represent each of the small regions corresponding to the numerical data allocated to each of the individual points. The step (2) may be performed between the step (1) and the step (5).

According to a first aspect of the present invention, a plurality of small regions are designated in a peripheral region of a three-dimensional compound structure. A numerical value is assigned to each of the small regions. In other words, unlike with the conventional CoMFA approach, which obtains information of a peripheral space of a three-dimensional compound structure as small number of "points information", the information in the peripheral space is obtained as much larger "regions" than that of the CoMFA approach. Thus, the information of the peripheral space of a compound can be represented by small number of numerical data (namely, with few dimensions) without the need to use the above-described PLS technique, which is used in the CoMFA approach. With the resultant numerical data, factor analysis that is most important for obtaining the correlation between a structure and activity can be performed by a linear multiple regression.

According to the first aspect of the present invention, since the information of small regions of the periphery of a three-dimensional compound structure is effectively converted into numerical data, the information can be obtained with much fewer dimensions than those according to the conventional CoMFA approach or the like. Thus, when information is represented by numerical data with few dimensions, a statistical problem (namely, "over estimation") can be prevented. In addition, since the numerical data with few dimensions can be directly used in an analyzing method such as the linear multiple regression method without the need to use a special technique for reducing dimensions of data, the factor analysis that is most important for obtaining the correlations between a structure and activity and the correlations between a structure and physical properties can be precisely performed. Thus, according to the first aspect of the present invention, the correlation between a three-dimensional structure and activity using three-dimensional structural information of a compound can be easily obtained. In addition, when an analysis for obtaining the correlation between a structure and activity is performed, the factor analysis power of the present invention provides scientists with very important information in comparison with the CoMFA method.

A second aspect of the present invention is a method for converting the interaction between a three-dimensional compound structure and a peripheral space thereof into numerical data, comprising the steps of (1) designating a peripheral region that includes the entire three-dimensional compound structure within the periphery thereof, (2) dividing the peripheral region into a plurality of small regions, (3) dividing the three-dimensional structure into a plurality of partial structures, (4) designating at least one virtual atom in each of the small regions, and (5) calculating the interactions between each of the atoms that comprise each of the partial structures obtained at the step (3) and at least one virtual atom in each of the small regions designated at step (4), and allocating the numerical data to the corresponding partial structure as a representative value of the partial structure. The step (3) may be performed before the step (1). Alternatively, the step (3) may be performed between the step (2) and the step (5).

According to the second aspect of the present invention, virtual atoms are placed on the periphery of a three-dimensional compound structure. The interactions between each of the virtual atoms and each of atoms that construct each of the partial structures of the three-dimensional compound structure are calculated (the interaction is, for example, steric or electrostatic interaction). Thus, the information of the interactions between a structure and each of the virtual atoms and pointcharge in the peripheral space can be obtained. Moreover, according to the second aspect of the present invention, the information of the interaction can be represented by small number of numerical data (having few dimensions), as with the first aspect of the present invention, the factor analysis that is most important for obtaining the correlations between a structure and activity can be performed corresponding to the linear multiple regression method, maintaining statistical reliability.

According to the second aspect of the present invention, the interaction between each of the partial structures that construct a three-dimensional compound structure and the peripheral environment can be effectively converted into numerical data. In addition, as with the first aspect of the present invention, the information of the interaction can be obtained having very few dimensions. Numerical data having very few dimensions can be directly used in an analyzing method such as the linear multiple regression method. Thus, factor analysis that is most important for obtaining the correlations between a structure and activity and the correlations between a structure and physico-chemical properties can be precisely performed. Consequently, the interaction between each of the partial structures of a compound and each of the virtual atoms and pointcharge on the periphery thereof, can be effectively converted into numerical data. This means that the special (three-dimensional) interactions between a compound and each of the virtual atoms on the periphery thereof can be objectively analyzed. Thus, it can be expected that the present invention can provide a significant advancement for scientific fields that study, for example, the correlations between a three-dimensional quantitative structure and activity based on the interactions between a ligand (a medicinal compound) and a receptor site (a working point of the medicinal compound in a human being) in designing drugs.

These and other objects, features and advantages of the present invention will become more apparent in light of the following detailed description of a best mode embodiment thereof, as illustrated in the accompanying drawings.

DESCRIPTION OF PREFERRED EMBODIMENTS

Next, with reference to the accompanying drawings, an embodiment of the present invention will be described.

Figure 3:
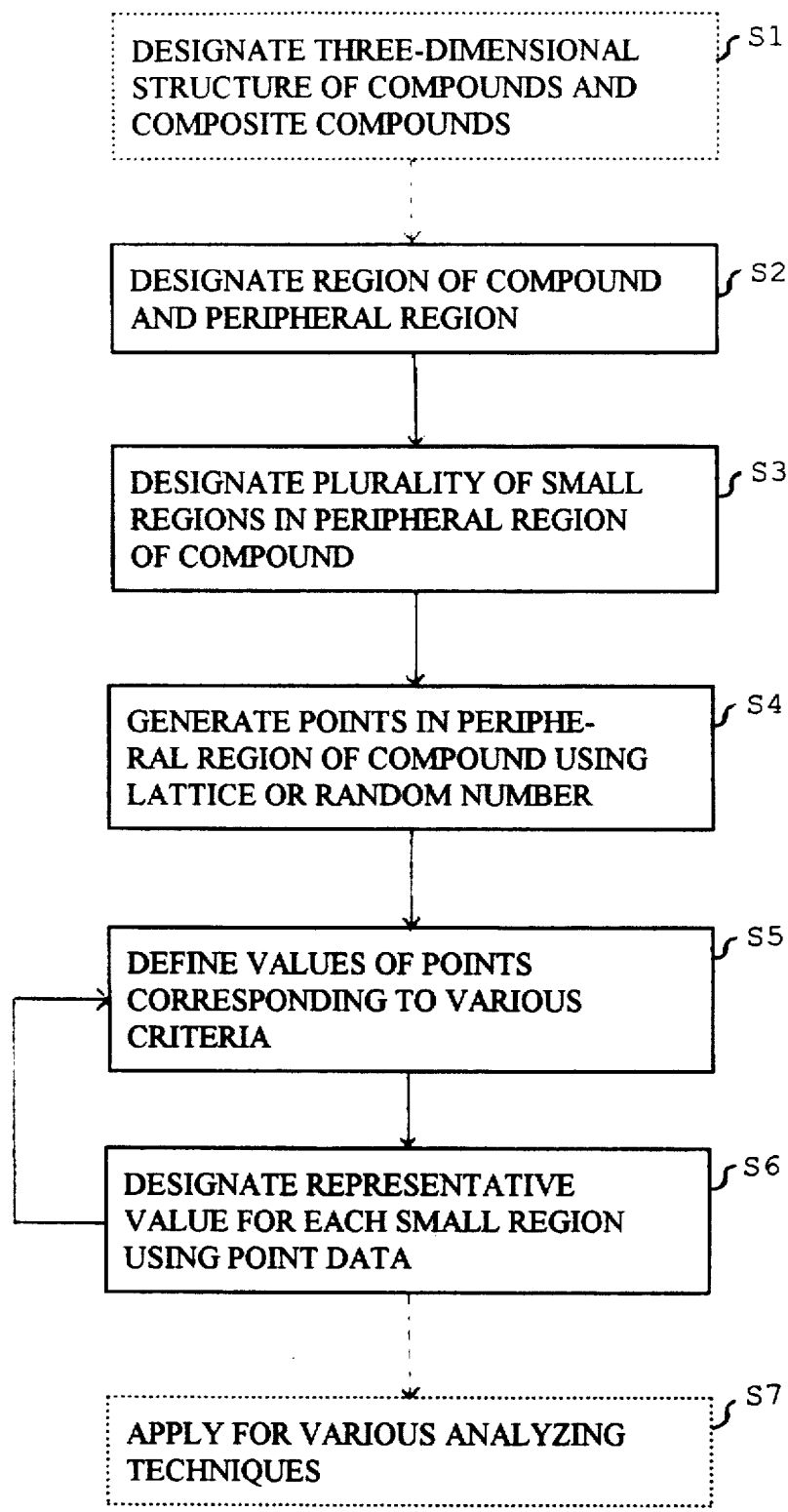
FIG. 3 is a flow chart showing a first embodiment of the present invention.

FIG. 3 is a flow chart showing a first embodiment of the present invention. In the flow chart, the processes of steps S2 to S6 accord with the first embodiment of the present invention.

In FIG. 3, before the processes (steps S2 to S6) of this embodiment are executed, a three-dimensional structure of a plurality of compounds is generated on, for example, common three-dimensional coordinates. Thereafter, molecules of the compounds are composed on the common three-dimensional coordinates (at step S1). In this embodiment, the three-dimensional structures can be designated by any conventional technique. Examples of the designating techniques are a technique for calculating three-dimensional coordinates corresponding to the molecular orbital method, molecular mechanics method, or the like, a technique using a database of three-dimensional structures, and so forth. In addition, a series of compounds can be composed on the common three-dimensional coordinates by any conventional technique. Examples of the superimposing techniques of compounds are a computer assisted superimposing technique using the least squares or simplex method, and a manual superimposing technique using a graphic display. After the three-dimensional compound structure is designated, the processes of this embodiment are performed.

Step S2 is a process for designating a region (inner region) of the three-dimensional compound structure and a peripheral region that includes the inner region is executed.

Figure 4:
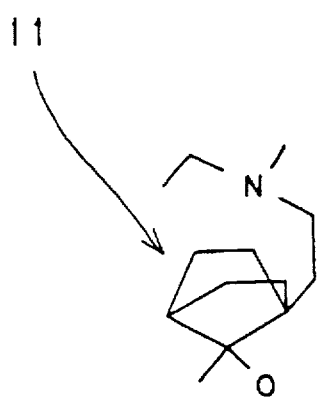
FIG. 4 is a schematic diagram showing an example of a three-dimensional compound structure.
Figure 5:
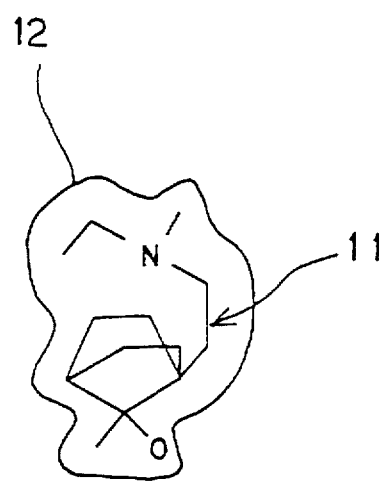
FIG. 5 is a schematic diagram showing an example of an inner region including a three-dimensional compound structure.
Figure 6:
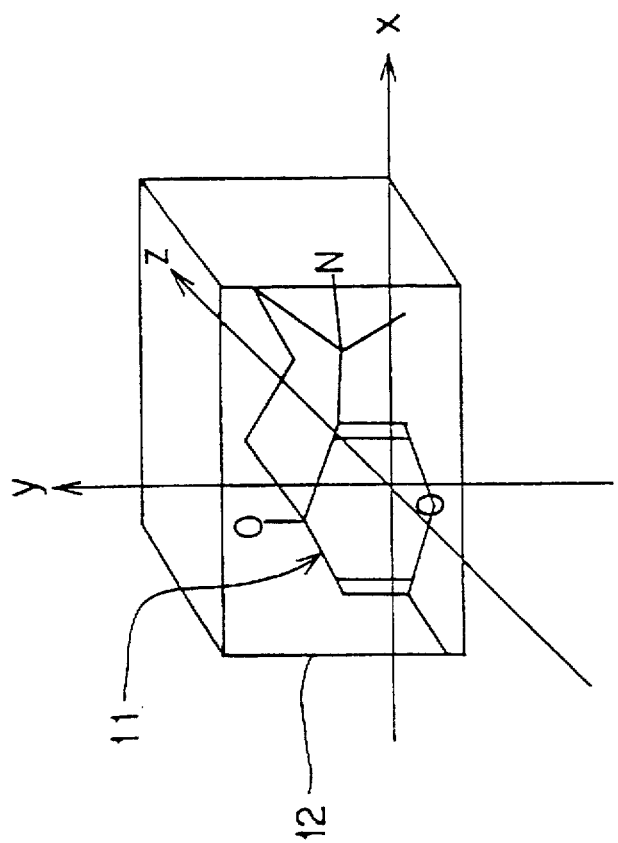
FIG. 6 is a schematic diagram showing another example of an inner region including a three-dimensional compound structure.
Figure 7:
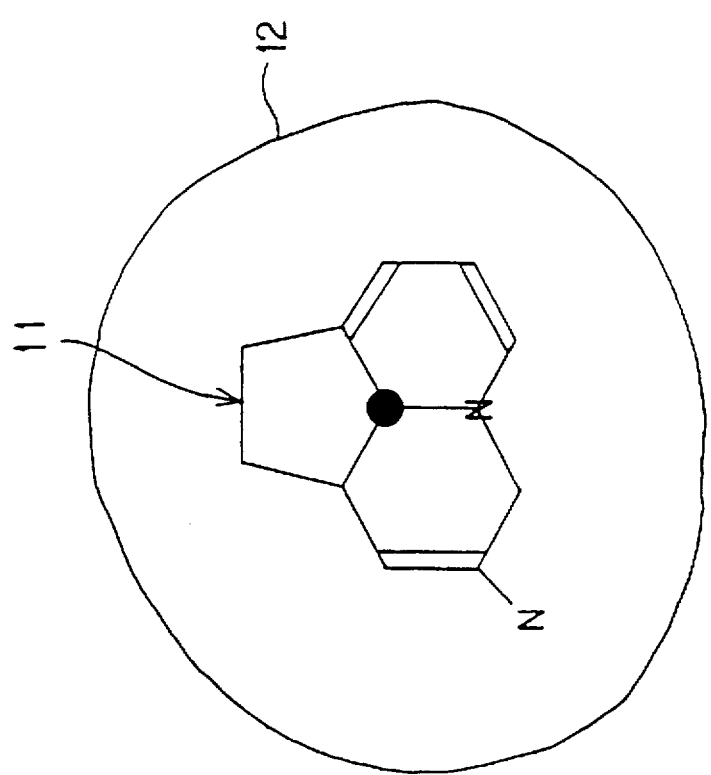
FIG. 7 is a schematic diagram showing a further example of an inner region including a three-dimensional compound structure.

In this embodiment, it is not necessary to cause the inner region to accord with the volume and shape of the three-dimensional structure. As a necessary condition, the inner region includes the entire structure. For example, a special filling chart produced using van der Waals radius data of atoms can be used as the inner region. For example, an inner region 12 shown in FIG. 5 can be designated for a three-dimensional compound structure 11 shown in FIG. 4. Alternatively, a special region of a compound can be designated for a three-dimensional shape such as a three-dimensional box or a sphere as an inner region. FIG. 6 shows an example of the inner region 12 that is designated by a rectangular box. FIG. 7 shows an example of the inner region 12 that is designated by a sphere. When the inner region is designated by a rectangular box, the maximum values and the minimum values of the X, Y, and Z coordinates are used. For example, when the maximum values and the minimum values of the X, Y, and Z coordinates are designated by 315, 169, 266, 53, and 247, 107, respectively, and a compound is placed in this box. When the inner region is designated by a sphere, the van der Waals surface of the furthest atom apart from the center of the sphere that is the center of gravity of the compound, is used as the radius of the sphere. Thus, the compound is placed in the sphere. It should be noted that the size and shape of the inner region can be automatically designated by a computer, or manually by a user with a graphic display.

Figure 8:
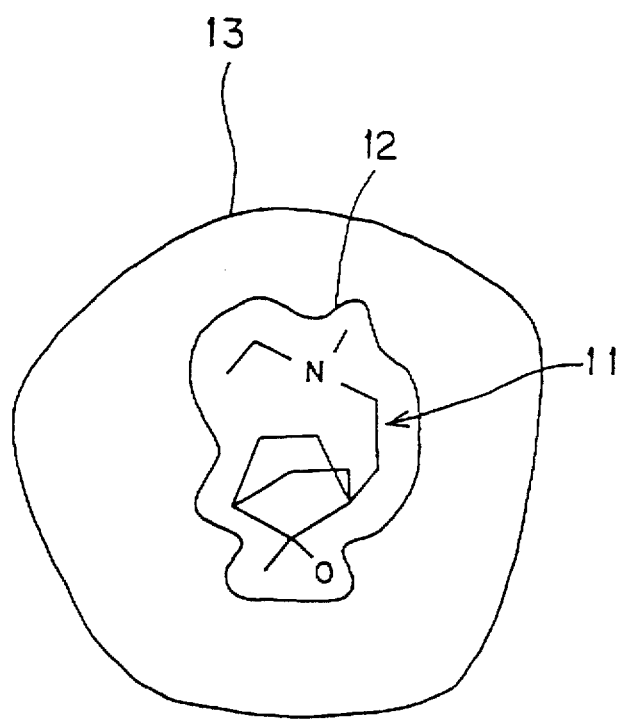
FIG. 8 is a schematic diagram showing a example of a peripheral region including an inner region.
Figure 9:
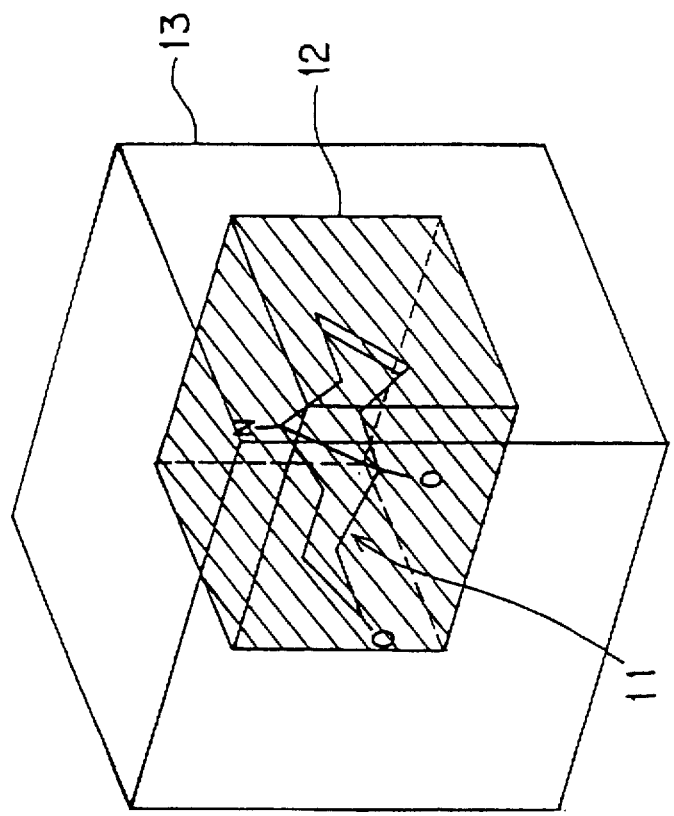
FIG. 9 is a schematic diagram showing another example of a peripheral region including an inner region.

It is also not necessary to cause the peripheral region to accord with the volume and shape of the structure, the same as with the inner region. Instead, as a necessary condition, the peripheral region surrounds the outer peripheral space of the inner region. In other words, the shape of the peripheral region may be a rectangular box, a cube, a sphere, an elliptical sphere, or the like that is larger than the inner region. For the inner region 12 (see FIG. 5) designated by a three-dimensional compound structure (see FIG. 4), a peripheral region 13 that has a different shape from that of the inner region 12 can be designated as shown in FIG. 8. Alternatively, for an inner region 12 of a box (see FIG. 9), a peripheral region 13 of a box can be designated. The user can input the width of a region for each coordinate directly or through a graphic display so as to designate the size, shape, and so forth of the peripheral region. As another alternative method, the width that is designated for each coordinate may be predetermined as a default value so as to automatically designate the outer space. As a further other method, a sphere or an ellipse that includes an inner box can be designated from the center of gravity of the box.

Figure 10:
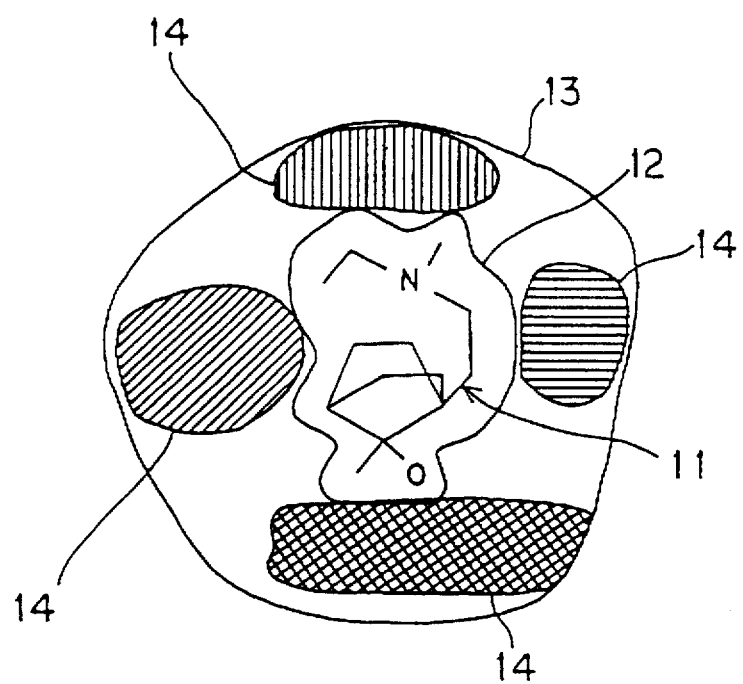
FIG. 10 is a schematic diagram showing an example of a small region designated in a peripheral region.

At step S3, a process for designating a plurality of small regions to be converted into numerical data in the peripheral region is executed. For example, a plurality of small regions 14, 14, ... (for example, the four small regions 14 shown in FIG. 10) are designated in the peripheral space 13. Although these small regions are preferably spaced a part from each other, a small overlapping thereof does not affect the analysis. The number of small regions to be designated depends on the compound group to be studied, the analysis level, or the like. Thus, the number of small regions is changed when necessary. Next, examples of the designating method for small regions will be described in detail.

Figure 11A:
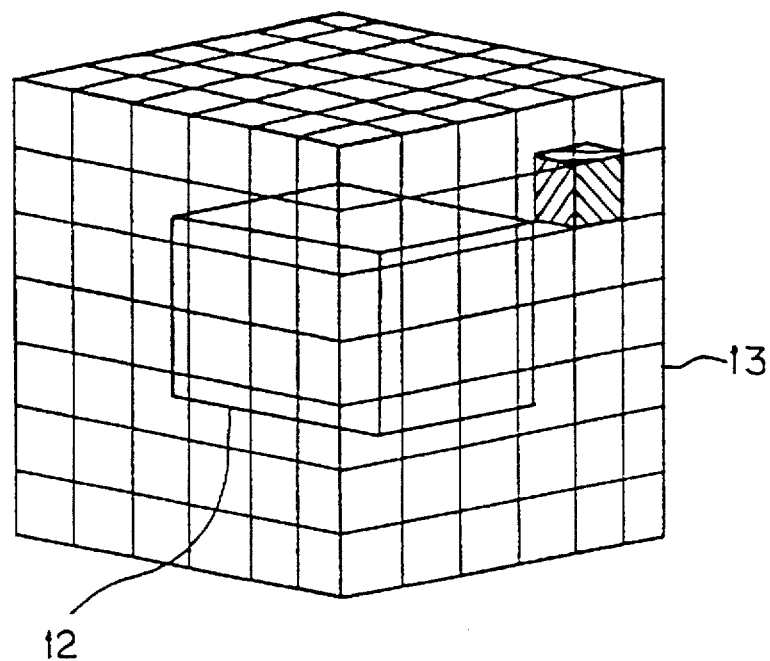
FIG. 11A is a schematic diagram showing a step for dividing a peripheral region and thereby designating a small region.
Figure 11B:
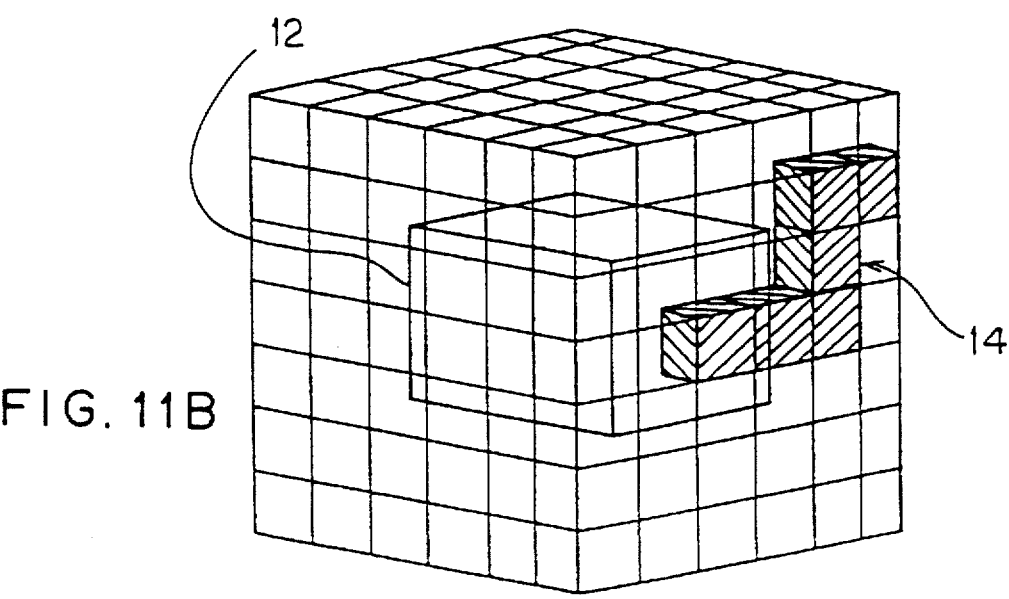
FIG. 11B is a schematic diagram showing a step for designating one of the small blocks divided at the step shown in FIG. 11A and thereby designating the small region.

As a first example for designating a plurality of small regions, as shown in FIGS. 11A and 11B, a box, a cube, a sphere, or the like that is displayed on a graphic display is manually designated. In other words, as shown in FIG. 11A, the three-dimensional space that constructs the peripheral region 13 is divided into small box or cubic boxes or spheres (in FIG. 11A, rectangular boxes). In this case, the size of blocks and spheres can be predetermined as a default value or calculated automatically by a computer. Thereafter, as shown in FIG. 11B, at least one desired box or sphere of the many divided boxes or spheres is designated so as to generate a small region 14 with the desired size and shape. At this point, when a desired region is designated from small boxes and spheres (see FIG. 11A), the designated boxes or spheres are treated as one region. Thus, any shape of small region (for example, region 14) can be generated.

Figure 12A:
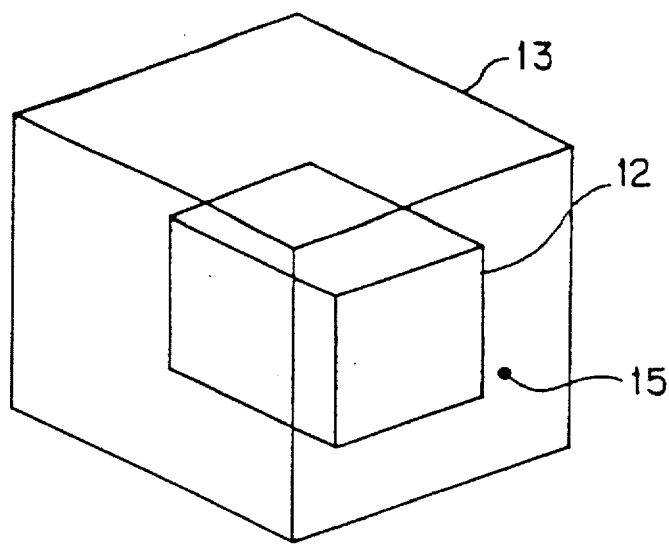
FIG. 12A is a schematic diagram showing a step for generating a point in a peripheral space for designating a small region and thereby designating the small region.
Figure 12B:
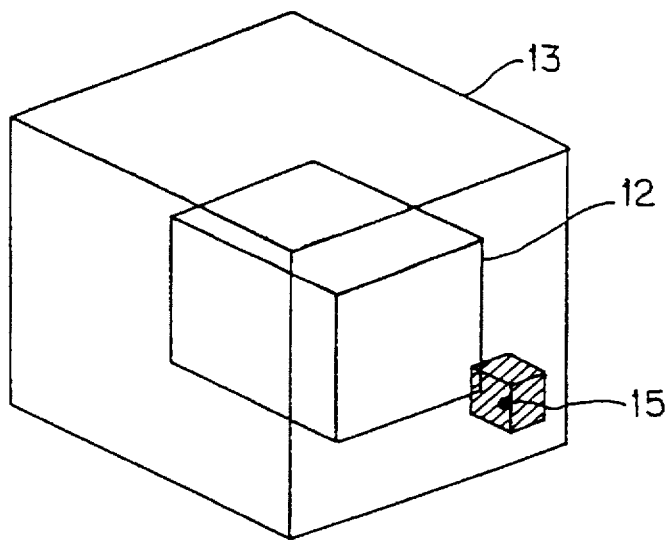
FIG. 12B is a schematic diagram showing a step for generating a block at the point generated at the step shown in FIG. 12A.
Figure 12C:
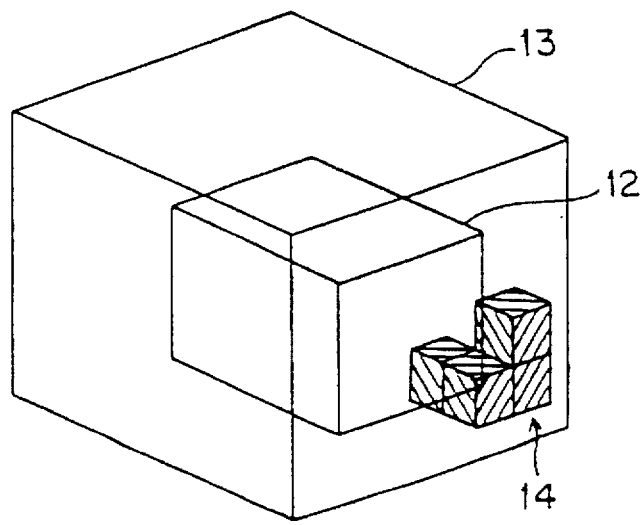
FIG. 12C is a schematic diagram showing a step for composing a plurality of blocks generated at the step shown in FIG. 12B and thereby designating a small region.

As a second example for designating a plurality of small regions, as shown in FIGS. 12A, 12B, and 12C, when a point (coordinate) 15 is manually designated in the peripheral region 13, boxes, spheres, or the like are formed around the point 15. The space of the boxes or spheres is treated as a small region 14. In other words, when the user designates the point 15 in the peripheral region 13 (see FIG. 12A), a box or a sphere is generated around the designated point 15 (see FIG. 12B in which a box is generated). Finally, as shown in FIG. 12C, by composing the boxes or spheres generated around a plurality of points 15, a small region 14 is generated.

Figure 13A:
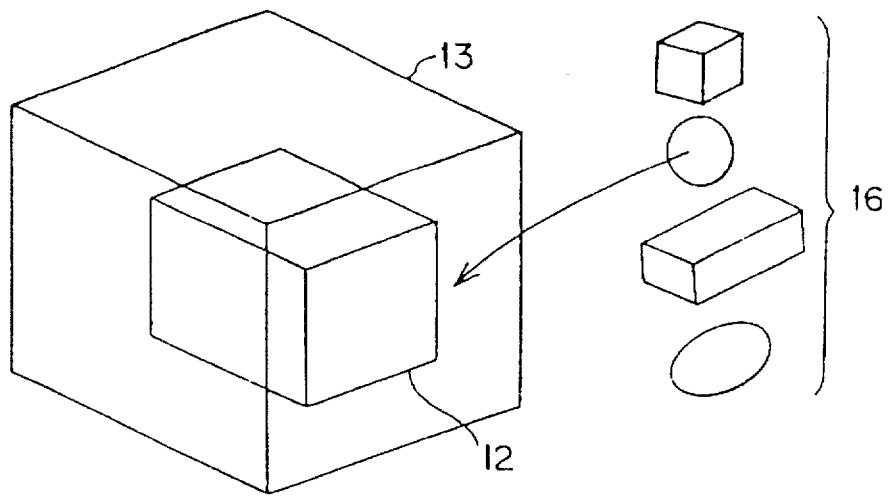
FIG. 13A is a schematic diagram showing a step for designating a desired one of several three-dimensional shapes and thereby designating a small region.
Figure 13B:
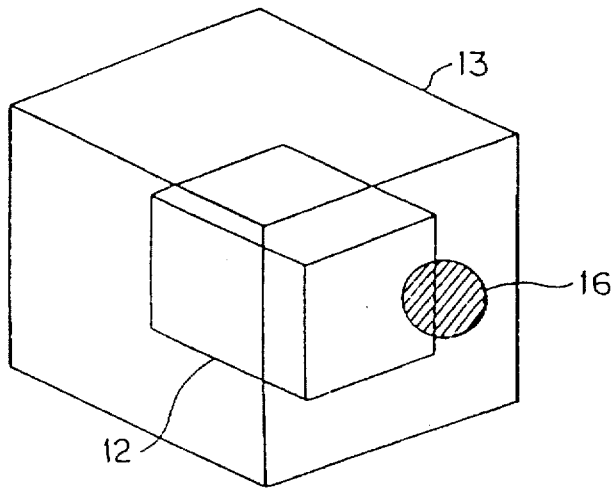
FIG. 13B is a schematic diagram showing a step for placing the part designated at the step shown in FIG. 13A in a peripheral space.
Figure 13C:
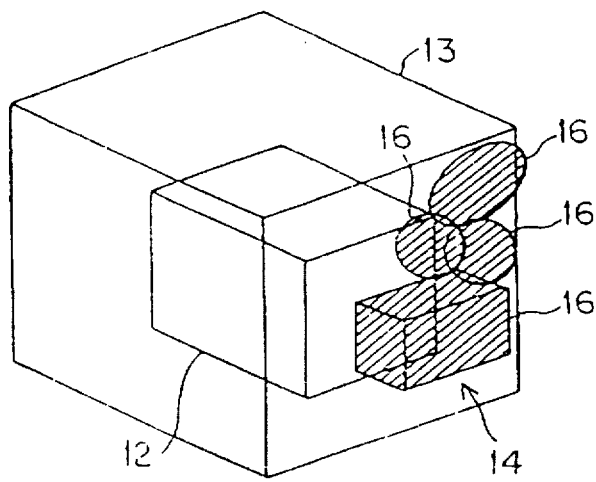
FIG. 13C is a schematic diagram showing a step for composing a plurality of parts designated at the step shown in FIG. 13B and thereby designating the small region.

As a third example for designating a plurality of small regions, as shown in FIGS. 13A, 13B, and 13C, three-dimensional components 16 that are three dimensional boxes, spheres, or the like are prepared. By filling a designated space with the components, a small region 14 can be formed. In other words, as shown in FIG. 13A, three-dimensional boxes, spheres, or the like that have a fixed shape or various shapes are prepared as components 16. When the user designates a desired one of the components 16 and places it in a suitable position of the peripheral region 13 as shown in FIG. 13B, the designated component becomes a component of a small region. When the user successively places a plurality of components 16, the entire region constructed of the components is treated as one region. Finally, as shown in FIG. 13C, a small region 14 is generated.

In the above-described examples, after a plurality of boxes or spheres are designated, they are composed. At this point, if the boxes or spheres are divided into a plurality of regions, they can be treated as a plurality of small regions.

Figure 14A:
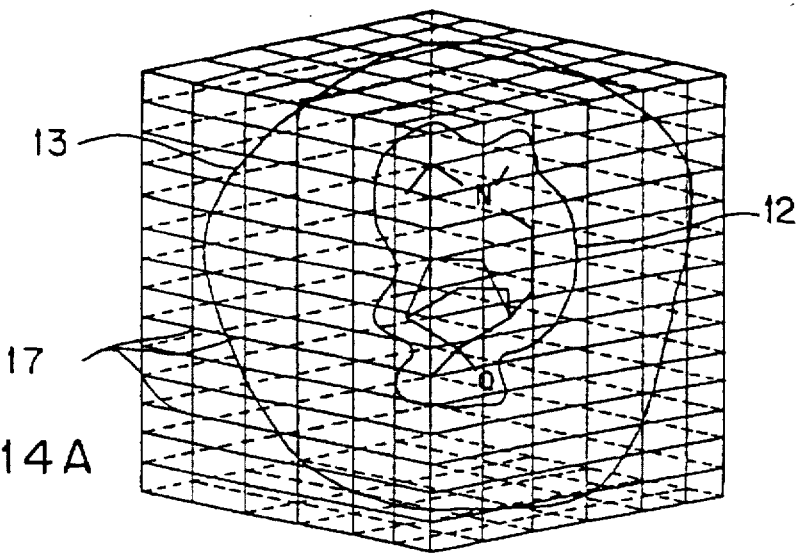
FIG. 14A is a schematic diagram showing a step for generating points in the entire peripheral region using a three-dimensional lattice.
Figure 14B:
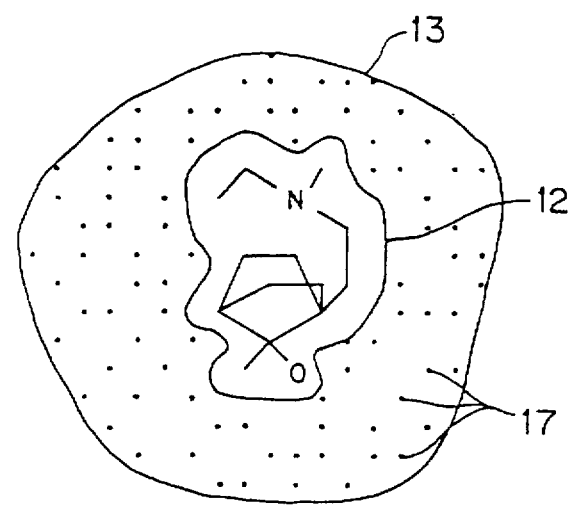
FIG. 14B is a schematic diagram showing a method for generating points in the entire peripheral region using random numbers.
Figure 14C:
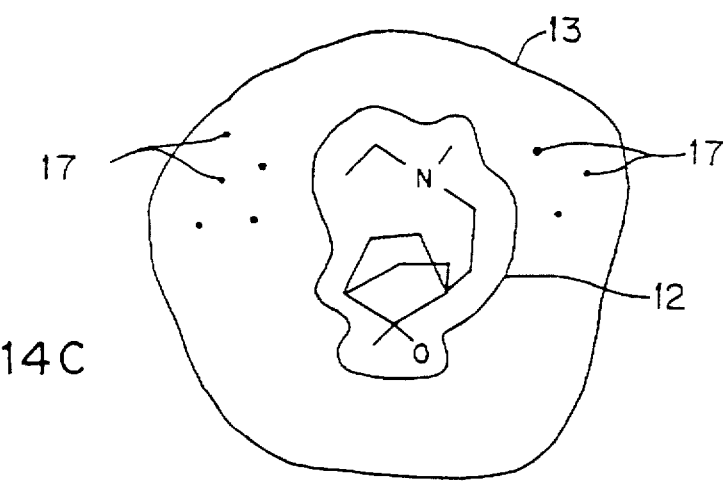
FIG. 14C is a schematic diagram showing a method for manually designating the position of a point and thereby generating a point in a peripheral region.
Figure 15A:
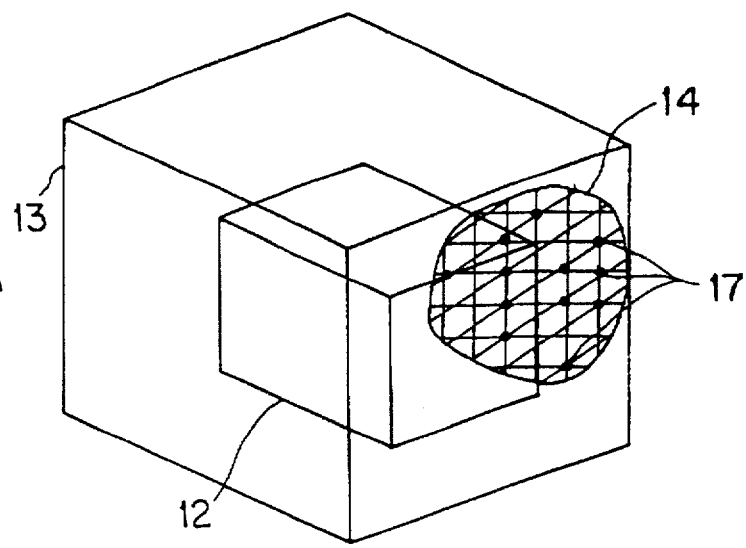
FIG. 15A is a schematic diagram showing a method for generating points only in a small region using a three-dimensional lattice.
Figure 15B:
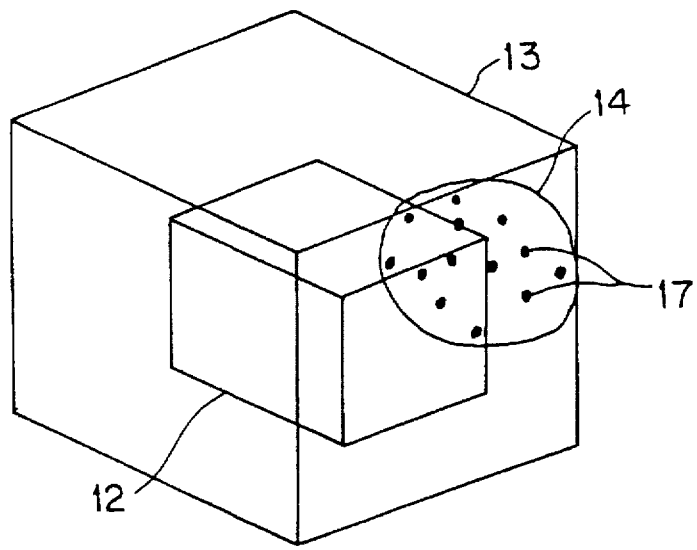
FIG. 15B is a schematic diagram showing a method for generating points only in a small region using random numbers.
Figure 15C:
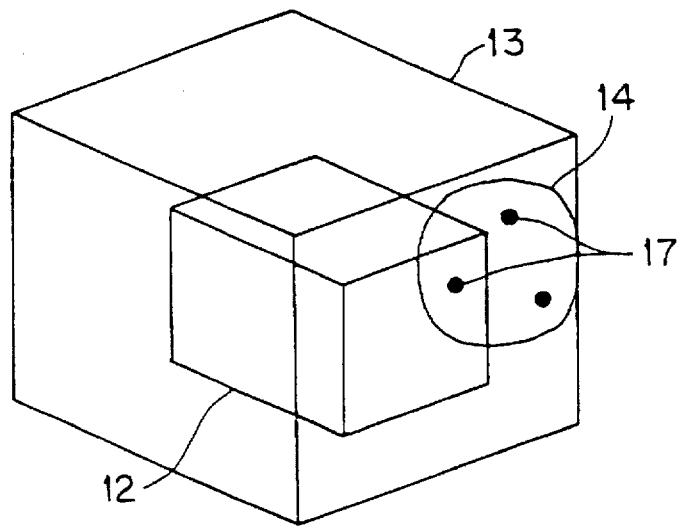
FIG. 15C is a schematic diagram showing a method for manually designating the positions of points and thereby generating points only in a small region.

After the small region is designated in the peripheral region, the process of step S4 shown in FIG. 3 is executed. In this process, many points are generated in the entire peripheral region designated at step S2 (when a small region has been designated, many points are generated in the small region). FIGS. 14A to 14C and 15A to 15C show examples of the method for generating such points. In the examples shown in FIGS. 14A to 14C, points are generated in the entire peripheral region 13. FIG. 14A shows the case that a three-dimensional lattice that surrounds the entire peripheral region 13 is generated, and individual lattice points are used as points 17 (the lattice pitch may be designated manually by the user or as a default value). FIG. 14B shows the case that points 17 are generated in the peripheral region 13 using random numbers (the number of points to be generated may be designated manually by the user or as a default value). FIG. 14C shows the case that points 17 are manually designated in the peripheral region 13 by the user. In examples shown in FIGS. 15A to 15C, points are generated in only a small region 14. As with the examples shown in FIGS. 14A, 14B, and 14C, FIG. 15A shows the case that a three-dimensional lattice is used, FIG. 15B shows the case that points are generated using random numbers, and FIG. 15C shows the case that points are manually designated by the user. When the three-dimensional lattice or random numbers are used, the points 17 should be equally distributed in the space. On the other hand, when the user, for example, a scientist manually designates points, he or she generates points with an intended deviation corresponding to his or her requirement depending on the background or specific purposes. The number of points generated in one small region is suitably selected when necessary. However, from view points of analysis, process, and computing speed, the number of points per small region is preferably 100 to 1000.

Figure 16:
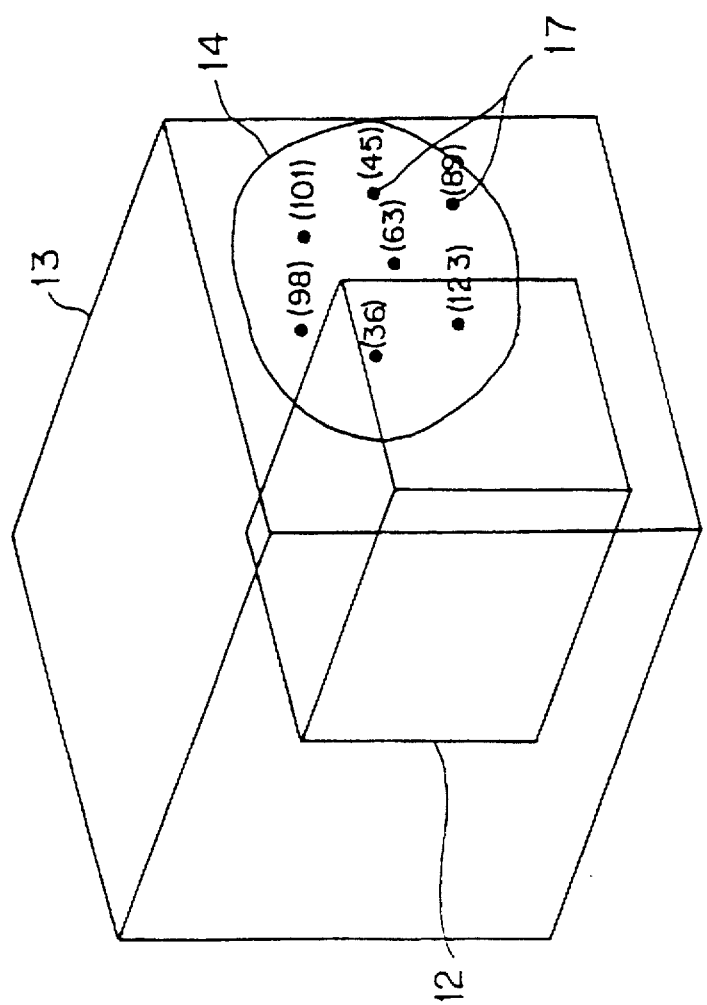
FIG. 16 is a schematic diagram showing an example of points to which numerical data are designated.

After the points are generated at step S4, the flow advances to step S5. At step S5, a process for designating values of individual points corresponding to various criteria is executed. In other words, the interaction between a three-dimensional compound structure and each of the points is calculated as numerical data. These numerical data are allocated to individual points. FIG. 16 shows the case that numerical data are allocated to individual points. Examples of numerical data to be calculated are the point charge in the molecular orbital method, repulsive force between molecules (attractive force or repulsive force of a virtual atom such as a carbon atom placed at a point against a compound), hydrophobic characteristic, volume, electrostatic interaction (attractive force or repulsive force of a charge (±) placed at a point against a compound), and the like.

Figure 17:
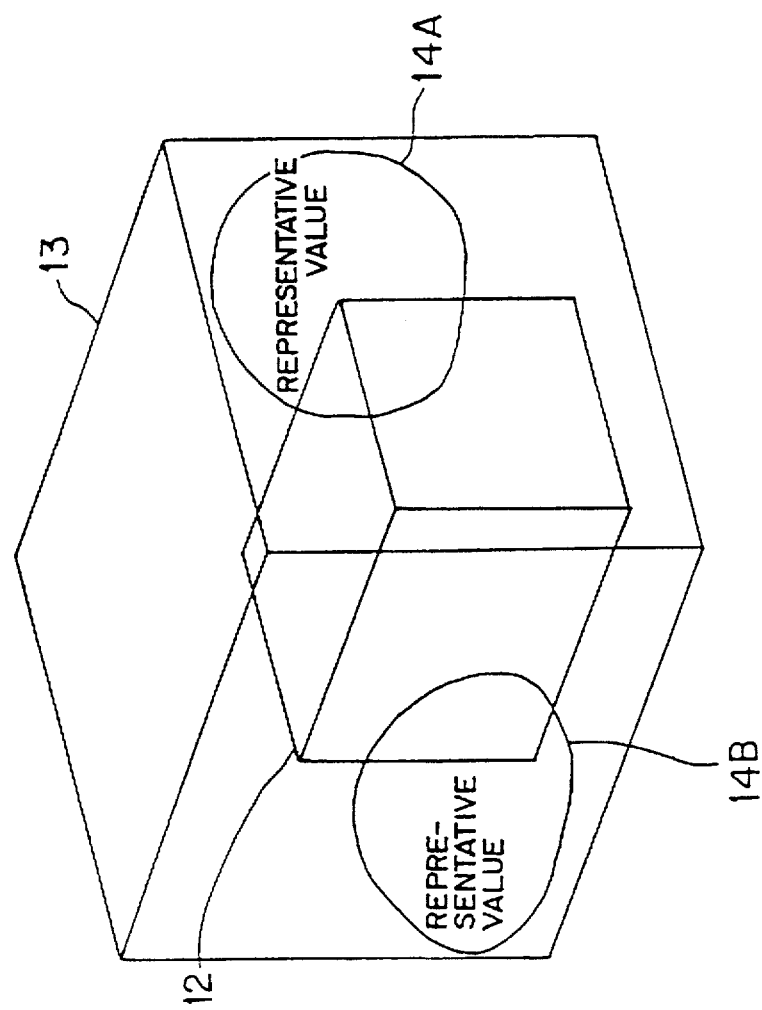
FIG. 17 is a schematic diagram showing an example of small regions to which representative values are designated.

Finally, the process of step S6 is executed. In this process, one or a plurality of numerical data that represent each small region (namely, representative values) are designated corresponding to the numerical data allocated to each point. Since a plurality of points 17 are present in each small region 14, a representative value is designated to each small region corresponding to numerical data allocated to these points. For example, in FIG. 17, numerical data (representative values) that represent two small regions 14A and 14B are designated. Examples of the representative values are the sum, the mean value, the maximum value, or the minimum value of numerical data allocated to all points in each small region 14, the sum of which is divided by the volume or the surface area of the small region, the value at the center of gravity of each small region 14, or the moment value of each small region (that are lengths of the X, Y, and Z axes from the center of gravity of the small region). In such a manner, one or a plurality of representative values (the number of representative values depends on the types of numerical data), the type of representative values, and the calculating method (for example, the average value of electron density, the maximum value of repulsive force, and so forth) are allocated to each small region. When the representative value of a new small region of numerical data of a different type allocated to each point is obtained, flow returns to step S5. At step S5, numerical data of each point is obtained.

In FIG. 3, the process of step S3 for designating a small region in a peripheral region is preceded by the process of step S2. However, it should be noted that the process of step 3 may also be preceded by the processes of step S4 or step S5.

When the representative value of each small region is obtained at steps S2 to S6 according to the embodiment, the representative value is supplied to a portion that performs various analyzing techniques, such as the linear multiple regression method, so as to analyze it (at step S7). Since such analyzing techniques are out of the scope of the present invention, their description is omitted.

Figure 1:
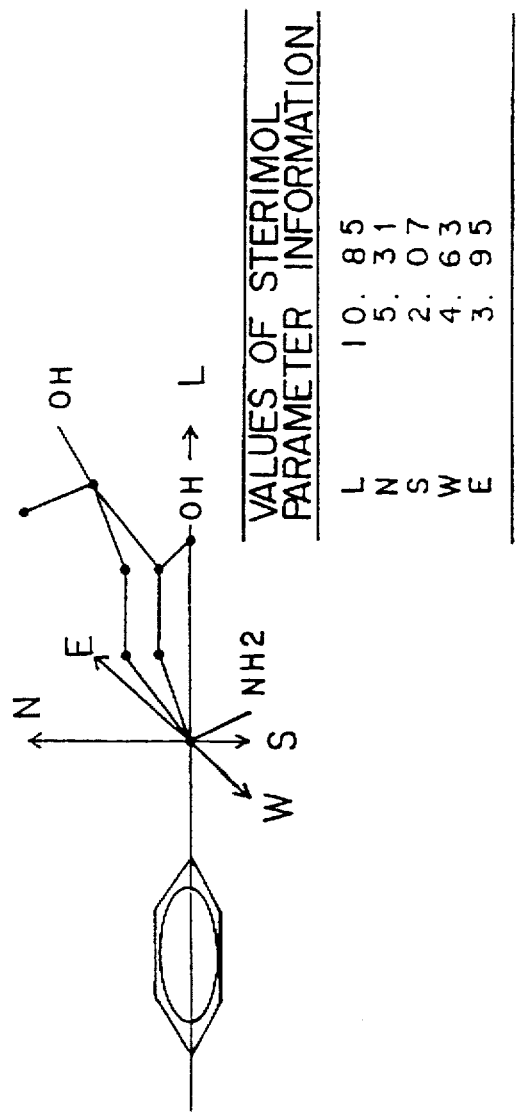
FIG. 1 is a schematic diagram showing an example of conventional STERIMOL parameter information.
Figure 2:
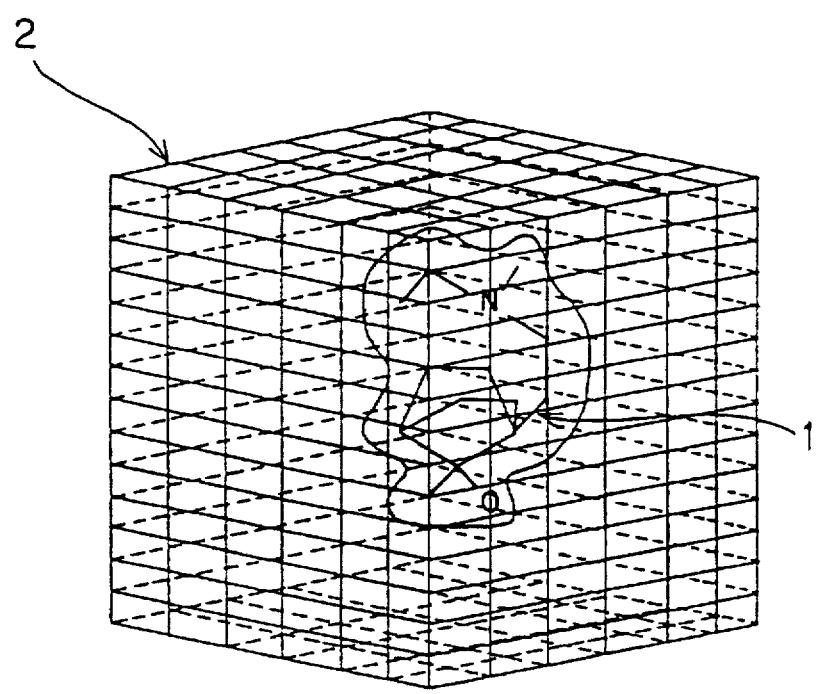
FIG. 2 is a schematic diagram showing an example of a three-dimensional lattice that is designated in a peripheral region of a three-dimensional compound structure corresponding to the conventional CoMFA approach.
Figure 18:
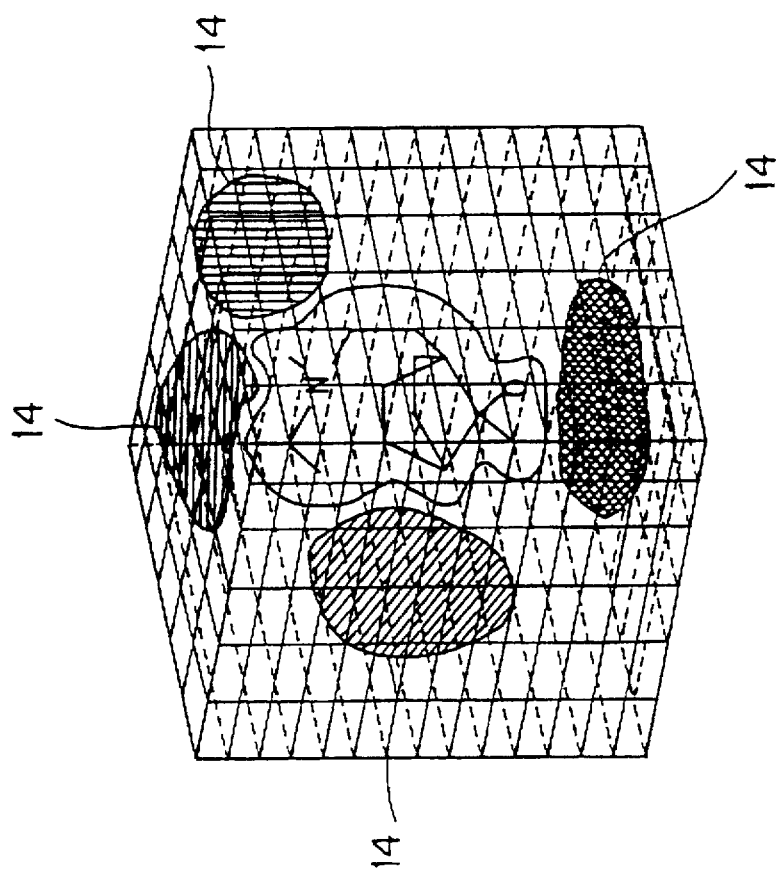
FIG. 18 is a schematic diagram showing an example of a three-dimensional lattice and small regions designated in a peripheral region of a three-dimensional compound structure according to the first embodiment of the present invention.

According to the method of the first embodiment, since information of each small region of the periphery of a three-dimensional compound structure is effectively converted into numerical data, the following effects can be accomplished. Since environmental information of the periphery of a compound is obtained for each small region, data with few dimensions can be obtained. Thus, the PLS technique for reducing the number of dimensions is not required, unlike with the conventional CoMFA method, that needs to use this technique. This is the strongest and most important feature of this patent. With respect to the number of dimensions, in the case of the CoMFA method, as shown in FIG. 2, information is obtained from all lattice points of the three-dimensional lattice. Therefore the CoMFA can not contain any information of small or local regions. However, according to this embodiment, as shown in FIG. 18, information of every small regions 14 is obtained. Thus, whereas the number of dimensions of the CoMFA method is as high as 1000 (at least 250 dimensions are required), the number of dimensions of this embodiment is the same as the number of small regions 14. Thus, the number of dimensions is several dimensions to several tens of dimensions (four dimensions are shown in FIG. 18). Consequently, in this embodiment, since numerical data is represented by data with few dimensions, the statistical problem (namely, the problem of "abundant estimation"), when limited information is represented by data with many dimensions, can be prevented. In addition, numerical data with few dimensions can be directly used for an analyzing technique such as the linear multiple regression method. Thus, according to this embodiment, factor analysis that is most important for obtaining the correlation between a structure and activity and the correlation between a structure and physicochemical properties, can be accurately performed. More specifically, in the CoMFA approach that is a technique for obtaining the correlation between a structure and activity using the information of a three-dimensional space, coefficients of a regression equation (for example A1, A2, and so forth of the equation (2)) do not have any meaning as information. However, according to this embodiment, individual coefficients of a regression equation have meaning as information.

Moreover, as a converting method of each small region into practical numerical data, various techniques (for example, the maximum value, the minimum value, the mean value, the value of the center of gravity, and so forth) can be used. Thus, numerical data can be used in various manners corresponding to the purpose of the analysis. Important information can be evaluated in smaller units as the maximum (minimum) value, the mean value, or the value of the center of gravity.

In addition, when a representative value of each small region is obtained, a technique for converting one small region into one numerical data, or another technique for converting one small region into a plurality of numerical data, can be used. When the entire compound is considered, the technique of one region to one data is important for performing factor analysis on a small region. On the other hand, when each small region is analyzed in detail, the technique of one region to a plurality of data can be used.

Figure 19:
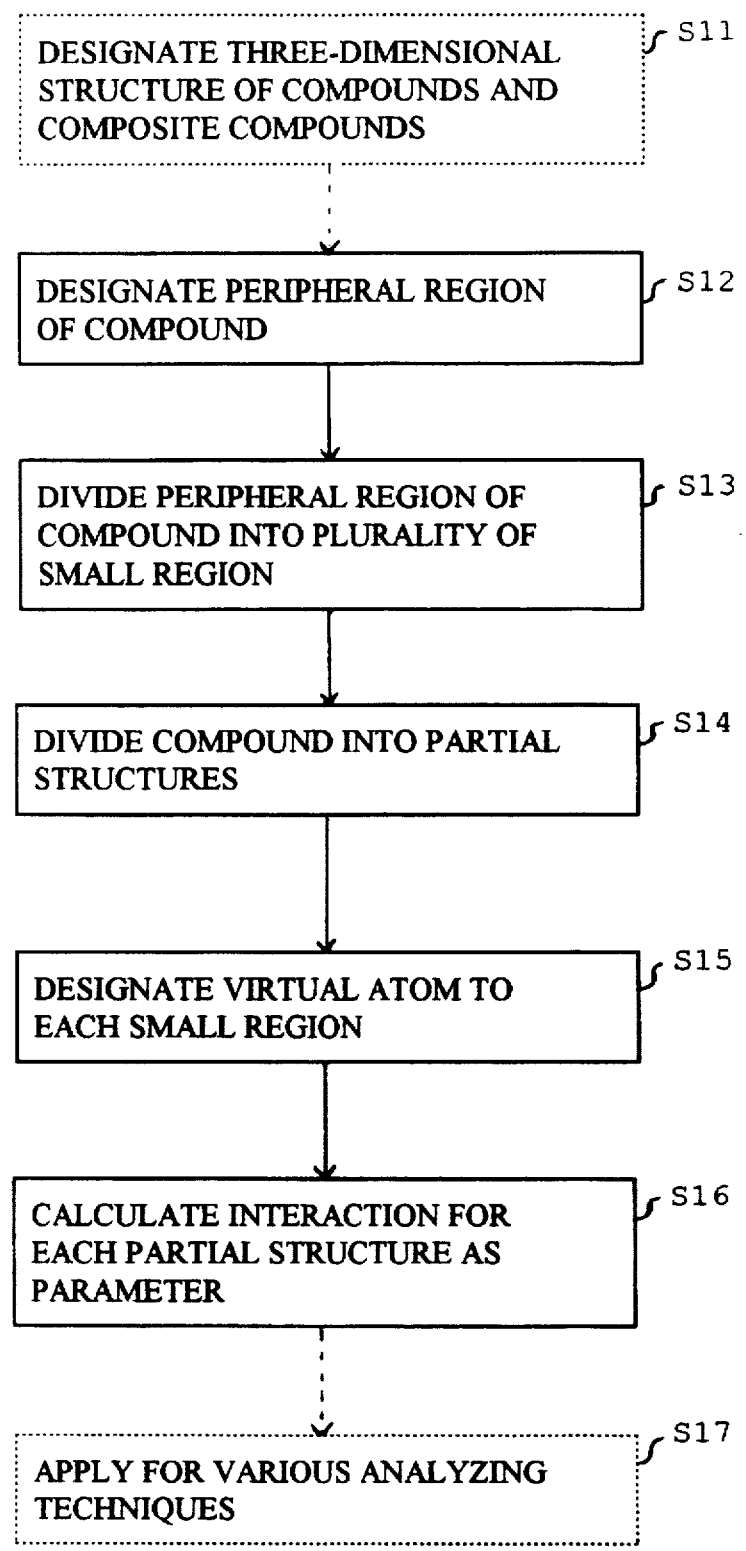
FIG. 19 is a flow chart showing a second embodiment of the present invention.

FIG. 19 is a flow chart showing a second embodiment of the present invention. The processes of steps S12 to S16 of the flow chart accord with the second embodiment.

In FIG. 19, before the processes of this embodiment (steps S12 to S16) are executed, a three-dimensional structure of a plurality of compounds is generated on common three-dimensional coordinates. Thereafter, molecules of the compounds are composed on the common three-dimensional coordinates (at step S11). This process is the same as the process at step S1 shown in FIG. 3. For simplicity, the description of this step is omitted. After the three-dimensional compound structure is determined, the processes according to this embodiment are performed.

Figure 20:
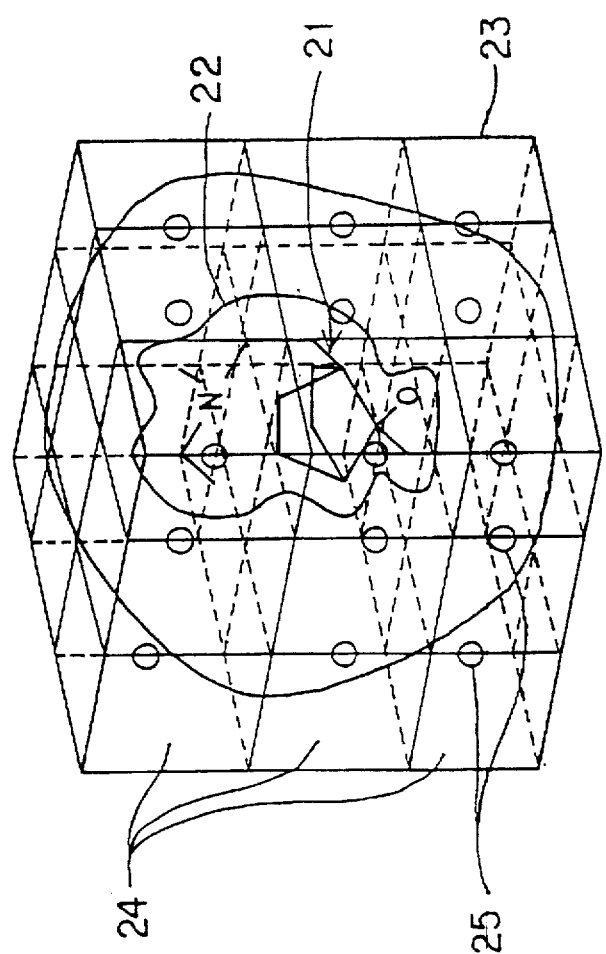
FIG. 20 is a schematic diagram showing an example of a three-dimensional lattice and virtual atoms designated in a peripheral region of a three-dimensional compound structure.

At step S12, a process for designating a region (inner region) of the three-dimensional compound structure, and for designating a peripheral region that includes the inner region, is performed. This process is the same as the process at step S2 shown in FIG. 3. It is not necessary to cause the inner region to accord with the volume and shape of the structure. Instead, as a necessary condition, the inner region includes the entire structure. For example, as shown in FIG. 20, an inner region 22 that surrounds a three-dimensional compound structure 21 can be designated. In addition, it is also not necessary to cause the peripheral region to accord with the volume and shape of the structure the same as with the inner region. As a necessary condition, the peripheral region surrounds the outer peripheral space of the inner region. For example, as shown in FIG. 20, a peripheral region 23 with a shape that is different from (or the same as) the shape of the inner region 12, can be designated to an inner region 22 designated for a three-dimensional compound structure 21.

Thereafter, at step S13, a process for dividing the peripheral region obtained at step S12 into a plurality of small regions is executed. In other words, as a preparation for placing virtual atoms on the periphery of a three-dimensional compound at step S15, a large peripheral region is divided into small regions. As long as the small regions are present between the compound structure and the peripheral region, they can be designated by any technique. For example, as shown in FIG. 20, when a three-dimensional lattice is designated in a peripheral region 23 (the shape of a box in FIG. 20), individual small blocks divided by the lattice elements are treated as the small regions 24.

Thereafter, the flow advances to step S14. At step S14, a process for dividing the three-dimensional compound structure into a plurality of partial structures is executed. In other words, by dividing the composed compound group at a plurality of positions, several smaller partial structures can be obtained. More accurately, the inner region obtained at step S12 is divided into several smaller regions. Structure in the divided regions are referred to as partial structures. For a specific technique for dividing one three-dimensional compound structure into a plurality of partial structures, refer to the above-described related art reference invented by the inventors of the present invention. The size of each partial structure should be greater than the sizes of the atoms that construct the compound. As long as each partial structure includes at least one atom, the compound structure can be divided at any position. In addition, the size, positions, quantity, and so forth of the partial structures can be manually designated by the user or automatically designated by a computer. In the former method, a technique for dividing a compound group into individual partial structures with a plurality of planes can be used. In the latter method, a technique for dividing a box including a compound group into small lattice elements, can be used.

Figure 21:
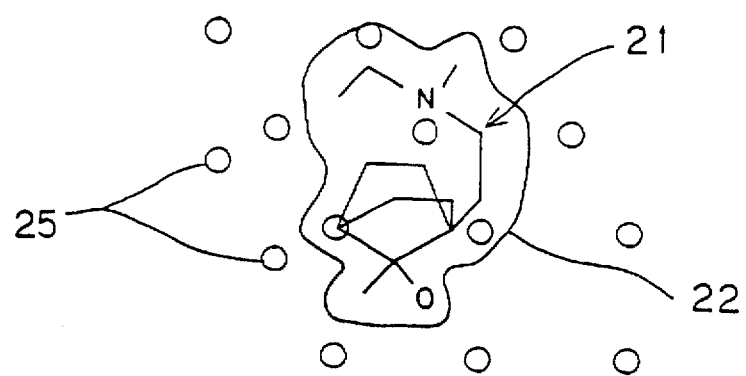
FIG. 21 is a schematic diagram in which the three-dimensional lattice is removed from the diagram shown in FIG. 20.

Thereafter, the flow advances to step S15. At step S15, a process for placing virtual atoms in each small region obtained at step S13 is executed. Examples of techniques for designating virtual atoms are a technique for placing a virtual atom 25 at the center point of each of a plurality of small regions 24, as shown in FIG. 20 (also shown in FIG. 21, with the three-dimensional lattice omitted), a technique for placing a plurality of virtual atoms in each of a plurality of small regions 24 at predetermined pitches, a technique for equally placing a plurality of virtual atoms in each of a plurality of small regions 24 using random numbers, a technique for manually placing virtual atoms, and the like. The types of virtual atoms depend on the types of numerical data to be analyzed. Normally, as virtual atoms, carbon atoms are used. Occasionally, other atoms may be used. For example, when the repulsive force between atoms is used as numerical data, carbon atoms can be used. When hydrogen bonding force or the like is used as numerical data, oxygen atoms or nitrogen atoms can be used. When electron-attracting force or repulsive force is used as numerical data, positive or negative charges can be used. In other words, the types of virtual atoms should be changed corresponding to the type of numerical data to be used. Thus, it is necessary to allow the types of virtual atoms to be changed corresponding to each type of numerical data.

After virtual atoms are designated to each small region, the flow advances to step S16. At step S16, a process for calculating the interaction between each atom that constructs each partial structure obtained at step S14, and each virtual atom designated at step S15 as numerical data, and for allocating the numerical data to the corresponding structure as its representative value, is executed. Examples of the interaction are the repulsive force energy between atoms and electronic interaction. The calculation should be repeated for each type of interaction. When the numerical data is calculated, there are many combinations of each partial structure and each virtual atom that are present in each small region. For example, a combination of one partial structure and one small region can be used. Alternatively, a combination of one partial structure and a plurality of small regions can be used. After the combination is designated, the interaction for each partial structure is obtained so as to calculate its representative value. Next, an example of the calculating method for each combination will be described.

In the case of the combination of one partial structure and one small region, for example, the interaction between each of the atoms that construct one partial structure and a virtual atom in one small region is calculated, and the sum for all the atoms is obtained as the representative value of the partial structure. As another example, the interaction between each of the atoms that construct one partial structure and each of the virtual atoms in one small region is calculated, and the sum of all the atoms is obtained as the representative value of the partial structure. As a further example, the interaction between each of the atoms designated by the user and each of the virtual atoms is calculated.

The case of the combination of one partial structure and a plurality of small regions, is substantially the same as the case of each of the above-described combinations. In other words, when a plurality of small regions for obtaining the interaction with a designated partial structure are designated, the same calculation as for the case of the combination of one partial structure and a plurality of small regions is performed. Finally, the sum of the obtained numerical values is treated as the representative value of the partial structure. Alternatively, the maximum value (or minimum value) or mean value of the obtained numerical values is treated as the representative value of the partial structure. However, in this case, there are several methods for selecting partial structures and small regions. For example, a method for using all small regions, a method for manually designating small regions, a method for automatically designating partial structures and small regions based on their distance by using a computer, namely, for calculating only atoms and virtual atoms which are located within a predetermined distance using a computer, and so forth.

In this embodiment, the process of step S14 for dividing a chemical structure into partial structures is preceded by the process of step S13 as shown in FIG. 19. However, it should be noted that the process of step S14 may be executed between the process of step S11 and the process of step S16.

After the representative values of the individual partial structures are obtained by the processes of steps S12 to S16, the resultant representative values are supplied to a portion that performs various analyzing techniques, such as the linear multiple regression method, and they are analyzed (at step S17). Since these analyzing techniques are out of the scope of the present invention, their description is omitted.

According to the method of the second embodiment, the interaction between each partial structure that constructs a three-dimensional compound structure and its peripheral environment can be effectively and quantitatively obtained. In addition, as with the first embodiment, the information of the interaction can be obtained with few dimensions. Thus, numerical data with few dimensions can be used for an analyzing technique such as the linear multiple regression method. Consequently, factor analysis that is most important for obtaining the correlation between a structure and activity and the correlation between a structure and physico-chemical properties can be precisely performed. As a result, the interaction between each of the partial structures and each of the atoms and electrons on the periphery thereof in a partial structural region of a compound, can be accurately obtained.

Although the present invention has been shown and described with respect to a best mode embodiment thereof, it should be understood by those skilled in the art that the foregoing and various other changes, omissions, and additions in the form and detail thereof may be made therein without departing from the spirit and scope of the present invention.

What is claimed is:

1. A method for converting information representing an interaction in a peripheral space of a three-dimensional compound structure into numerical data, comprising the steps of:
   (1) designating a peripheral region that includes the entire three-dimensional compound structure on the periphery thereof;
   (2) designating a plurality of small regions in the peripheral region;
   (3) generating a plurality of points in the peripheral region;
   (4) calculating the interaction between the three-dimensional compound structure and each of points in the small regions to produce numerical data corresponding to each point;
   (5) generating numerical data that represents each of the small regions based on the numerical data corresponding to each point calculated in step (4).

2. The method as set forth in claim 1, wherein step (3) is performed by dividing the peripheral region using a three-dimensional lattice and treating each lattice point that is uniformly present in the three-dimensional lattice as one point.

3. The method as set forth in claim 1, wherein step (3) is performed by uniformly generating a plurality of points in the peripheral region using random numbers.

4. The method as set forth in claim 1, wherein the interaction calculated as the numerical data in step (4) is at least one of a point charge in molecular orbital method, repulsive force or interaction energy between atoms, hydrophobic characteristic, volume, and electrostatic interaction.

5. The method as set forth in claim 1, wherein the numerical data that represents each of the small regions generated in step (5) is the sum of the numerical data corresponding to each of the points of each of the small regions.

6. The method as set forth in claim 1, wherein the numerical data that represents each of the small regions generated in step (5) is the mean value of the numerical data corresponding to each of the points of each of the small regions.

7. The method as set forth in claim 1, wherein the numerical data that represents each of the small regions generated in step (5) is a value of which the sum of the numerical data corresponding to each of the points of each of the small regions is divided by one of the volumes and the surface area of each of the small regions.

8. The method as set forth in claim 1, wherein the numerical data that represents each of the small regions generated in step (5) is a value of which the sum of the numerical data corresponding to each of the points of each of the small regions is divided by one of the volume and the surface area of each of the small regions.

9. A method for converting the interaction between a three-dimensional compound structure and a peripheral space thereof into numerical data, comprising the steps of:
   (1) designating a peripheral region that includes the entire three-dimensional compound structure on the periphery thereof;
   (2) dividing the peripheral region into a plurality of small regions;
   (3) dividing the three-dimensional structure into a plurality of partial structures;
   (4) designating at least one virtual atom in each of the small regions; and
   (5) calculating the interaction between each of the atoms that construct each of the partial structures obtained at said step (3) and the virtual atom in at least one of the small regions designated at said step (4) to produce numerical data representative of the partial structure.

10. The method as set forth in claim 9, wherein step (4) is performed by designating one virtual atom at the center point of each of the small regions obtained at said step (2).

11. The method as set forth in claim 9, wherein step (4) is performed by designating a plurality of virtual atoms in each of the small regions obtained in step (2) at predetermined intervals.

12. The method as set forth in claim 9, wherein step (4) is performed by equally placing a plurality of virtual atoms in the peripheral region obtained in step (1) using random numbers so as to place at least one virtual atom in each of the small regions.

13. The method as set forth in claim 9, wherein the interaction calculated as the numerical data in step (5) is at least one of repulsive force or interaction energy between atoms an electronic interaction.

14. The method as set forth in claim 9, wherein the numerical data allocated to each of the partial structures as the representative value in step (5) is the sum of the interaction between each of the atoms that construct each of the partial structures and at least one virtual atom in each of the small regions.

15. The method as set forth in claim 9, wherein the numerical data allocated to each of the partial structures as the representative value in step (5) is one of the maximum value and the minimum value of the interaction between each of the atoms that construct each of the partial structures and at least one virtual atom in each of the small regions.

16. The method as set forth in claim 9, wherein the numerical data allocated to each of the partial structures as the representative value in step (5) is the mean value of the interaction between each of the atoms that construct each of the partial structures and at least one virtual atom in each of the small regions.

* * * * *